United States Patent
Link et al.

(10) Patent No.: US 12,257,155 B2
(45) Date of Patent: *Mar. 25, 2025

(54) MODULAR ENDOPROSTHESIS SHAFT SYSTEM WITH ROTATION ELEMENT

(71) Applicant: Waldemar Link GmbH & Co. KG, Hamburg (DE)

(72) Inventors: Helmut D. Link, Hamburg (DE); Udo Borchers, Norderstedt (DE); Gunnar Erb, Hamburg (DE)

(73) Assignee: Waldemar Link GmbH & Co. KG, Hamburg (DE)

( * ) Notice: Subject to any disclaimer, the term of this patent is extended or adjusted under 35 U.S.C. 154(b) by 121 days.

This patent is subject to a terminal disclaimer.

(21) Appl. No.: 18/301,873

(22) Filed: Apr. 17, 2023

(65) Prior Publication Data
US 2023/0285157 A1 Sep. 14, 2023

Related U.S. Application Data

(63) Continuation of application No. 16/772,766, filed as application No. PCT/EP2018/084335 on Dec. 11, 2018, now Pat. No. 11,654,029.

(30) Foreign Application Priority Data

Dec. 15, 2017 (EP) ..................................... 17207776

(51) Int. Cl.
*A61F 2/36* (2006.01)
*A61F 2/30* (2006.01)

(52) U.S. Cl.
CPC .. *A61F 2/3672* (2013.01); *A61F 2002/30365* (2013.01); *A61F 2002/30367* (2013.01);
(Continued)

(58) Field of Classification Search
CPC ............ A51F 2/3672; A51F 2002/3674; A51F 2002/3035; A51F 2002/30474; A51F 2002/30494
See application file for complete search history.

(56) References Cited

U.S. PATENT DOCUMENTS 4,676,797 A * 6/1987 Anapliotis ............ A61F 2/4637
623/23.45
5,507,817 A * 4/1996 Craig .................... A61F 2/4014
623/20.11
(Continued)

FOREIGN PATENT DOCUMENTS

DE 4320086 A1 * 12/1994 ......... A61F 2/30739
DE 19517275 A1 * 11/1996 ......... A61F 2/30739
(Continued)

OTHER PUBLICATIONS

Search Report mailed Mar. 23, 2021, in connection with Russian Patent Application No. 2020123102, 4 pgs (including translation).
(Continued)

*Primary Examiner* — Alvin J Stewart
(74) *Attorney, Agent, or Firm* — Chiesa Shahinian & Giantomasi PC

(57) ABSTRACT

The invention relates to an endoprosthesis shaft system for elongate bones, comprising an anchoring part and a shaft, which is formed from module elements that can be coupled by means of a plug-in connection, wherein a mutual rotation of the elements along the shaft is adjustable and is blocked by means of an anti-rotation mechanism. In order to adjust the rotation, a rotation piece is provided as a further module element, which has a self-contained rotation adjustment device and a clamping device as a mechanism for blocking the rotation. The rotation piece comprises two end faces for the plug-in connection and a sleeve. The invention provides, with the rotation piece, a particular module element for the
(Continued)

shaft, which as a structural unit allows both an adjustment of the rotation and a blocking against undesired rotation in a self-contained unit.

20 Claims, 3 Drawing Sheets

(52) U.S. Cl.
CPC .............. *A61F 2002/30474* (2013.01); *A61F 2002/3674* (2013.01)

(56) References Cited

U.S. PATENT DOCUMENTS

| | | | |
|---|---|---|---|
| 5,620,445 A | | 4/1997 | Brosnahan et al. |
| 5,653,765 A | | 8/1997 | McTighe et al. |
| 6,102,956 A | * | 8/2000 | Kranz ................... A61F 2/3662 623/23.15 |
| 6,436,144 B1 | * | 8/2002 | Ahrens ................. A61F 2/4059 623/19.11 |
| 6,613,092 B1 | * | 9/2003 | Kana ................... A61F 2/30942 623/23.45 |
| 7,235,106 B2 | | 6/2007 | Daniels et al. |
| 7,507,256 B2 | | 3/2009 | Heck et al. |
| 7,867,282 B2 | * | 1/2011 | Heck ........................ A61F 2/28 606/62 |
| 7,959,639 B1 | | 6/2011 | McGovern et al. |
| 7,998,217 B1 | | 8/2011 | Brown |
| 7,998,218 B1 | * | 8/2011 | Brown .................... A61F 2/385 623/20.14 |
| 8,100,982 B2 | * | 1/2012 | Heck ........................ A61F 2/28 623/20.35 |
| 8,252,002 B2 | * | 8/2012 | Huff ...................... A61F 2/4684 606/62 |
| 8,496,711 B2 | | 7/2013 | Anapliotis et al. |
| 8,518,122 B2 | * | 8/2013 | Anapliotis ................ A61F 2/30 623/22.42 |
| 8,721,729 B1 | * | 5/2014 | Lu .......................... A61F 2/389 623/20.15 |
| 9,144,506 B2 | * | 9/2015 | Phelps ................... A61F 2/4611 |
| 9,168,156 B2 | | 10/2015 | Crabtree et al. |
| 9,597,203 B2 | * | 3/2017 | Emerick ................... A61F 2/40 |
| 11,654,029 B2 | * | 5/2023 | Link ...................... A61F 2/3672 623/22.42 |
| 2004/0122525 A1 | * | 6/2004 | Daniels ................. A61F 2/4684 623/22.42 |
| 2005/0071014 A1 | * | 3/2005 | Barnett ..................... A61F 2/40 623/23.45 |
| 2005/0187637 A1 | | 8/2005 | Karrer et al. |
| 2019/0053836 A1 | * | 2/2019 | Sweeney ............ A61B 17/7013 |
| 2020/0306049 A1 | * | 10/2020 | Link ...................... A61F 2/3672 |
| 2022/0401219 A1 | * | 12/2022 | Link ....................... A61L 27/56 |
| 2024/0065848 A1 | * | 2/2024 | Clevett ............... A61F 2/30734 |

FOREIGN PATENT DOCUMENTS

| | | | | |
|---|---|---|---|---|
| DE | 19735875 A1 | * | 3/1999 | .......... A61F 2/3662 |
| DE | 102004052143 A1 | | 5/2005 | |
| EP | 2907480 A1 | | 8/2015 | |
| JP | H10-502284 A | | 3/1998 | |
| JP | 2004-202234 A | | 7/2004 | |
| RU | 122017 U1 | | 11/2012 | |
| WO | 1996/01086 A1 | | 1/1996 | |
| WO | 2006065768 A2 | | 6/2006 | |
| WO | 2006065880 A2 | | 6/2006 | |
| WO | 2007028832 A2 | | 3/2007 | |
| WO | 2007028832 A3 | | 7/2007 | |
| WO | 2010020429 A1 | | 2/2010 | |
| WO | WO-2021053004 A1 | * | 3/2021 | ......... A61F 2/30734 |

OTHER PUBLICATIONS

Notice of Reasons for Refusal mailed Jun. 28, 2022, in connection with Japanese Patent Application No. 2020-531987, 8 pgs (including translation).

English Translation of the International Preliminary Report on Patentability issued on Jun. 16, 2020, in connection with International Patent Application No. PCT/EP2018/084335.

* cited by examiner

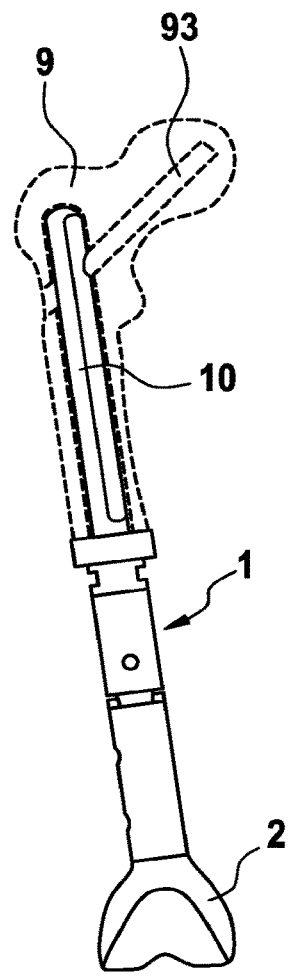 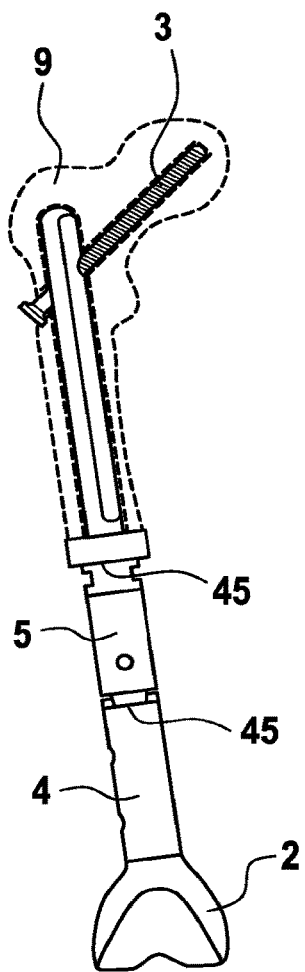 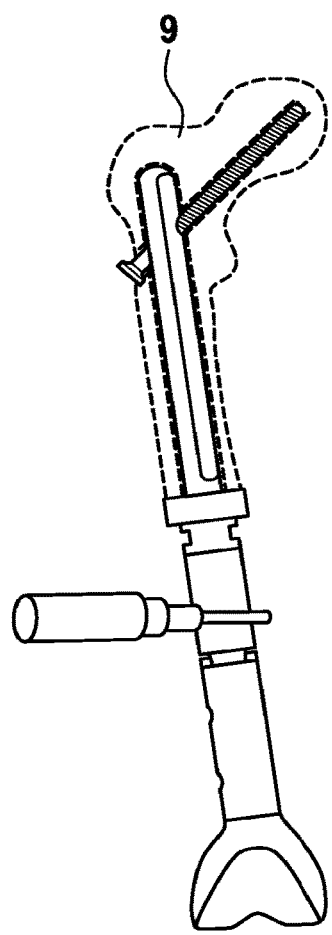
Fig. 1a  Fig. 1b  Fig. 1c

MODULAR ENDOPROSTHESIS SHAFT SYSTEM WITH ROTATION ELEMENT

CROSS-REFERENCE TO RELATED APPLICATIONS

This application is a Continuation of prior-filed U.S. Utility patent application Ser. No. 16/772,766, filed Jun. 12, 2020, which is a National Stage Entry of PCT/EP2018/084335, filed on Dec. 11, 2018, which claims priority to European Patent Office Application 17207776.0, filed on Dec. 15, 2017; the entire disclosures of all of which are incorporated by reference herein.

FIELD

The invention relates to an endoprosthesis for elongate bones, comprising a modular shaft system. The modular shaft system comprises a plurality of elements to be coupled by means of a plug-in connection. In order to adjust a mutual rotation of the elements relative to one another, a rotation element is provided, wherein a position that is thereby adopted is fixed by means of an anti-rotation mechanism acting with form-fit engagement.

BACKGROUND

Endoprostheses are retained in the bone by means of an anchoring part and have shafts for supporting joint components or for replacing defective bone parts. Depending on the particular use, the shaft in question can be of a considerable length. To be able to cover different lengths using a manageable number of different elements, modular systems have been developed. These modular systems comprise a plurality of elements that can be plugged together, wherein conical couplings are in most cases provided as plug connections. These each comprise a conical stub and a conical sleeve which, in the state when plugged together, generally hold sufficiently firmly to each other in order to be able to transmit axial forces, and also rotational forces, safely and without displacement.

During the implantation of such an endoprosthesis, there is sometimes a need to rotate the shaft to a defined and anatomically favorable orientation. This may be required so that a prosthesis head, arranged at one end of the shaft, can be brought into a favorable direction. In known modular shaft systems (for example the Megasystem C sold by the Link company, Hamburg, Germany), the individual components of the shaft can be connected to one another in any desired rotational orientation, specifically thanks to the superb plug connection, but a correction of the relative rotation between the individual components is difficult after the connection has been made. Moreover, a modular prosthesis system is known (for example the MUTARS system sold by the company implantcast, Buxtehude, Germany) in which a screw fitting is guided centrally along the shaft axis for securing purposes. By loosening this screw fitting, it is possible for the individual elements to be rotated relative to one another, and, once said screw fitting has been tightened, the elements connected by toothed engagement are blocked in rotation. However, the actuation requires that the upper end and lower end of the shaft are accessible. This is often no longer the case after the implantation.

The object of the invention is to make available an improved shaft system for an endoprosthesis that avoids these disadvantages.

The solution according to the invention lies in the features of the independent claim. Advantageous developments are the subject matter of the dependent claims.

In an endoprosthesis shaft system for elongate bones, comprising an anchoring part and a shaft, which is formed from module elements that can be coupled by means of a plug connection, wherein a mutual rotation of the elements along the shaft is adjustable and is blocked by means of an anti-rotation mechanism, provision is made according to the invention that, in order to adjust the rotation, a rotation piece is provided as a further module element, which has a self-contained rotation adjustment device and a clamping device as a means for blocking the rotation, wherein the rotation piece has two end faces, for the plug connection, and a jacket.

With the rotation piece, the invention provides a special module element for the shaft, which module element, as a structural unit, permits a rotational adjustment and also blocks against undesired rotation, in one self-contained unit. By the configuration as an intermediate piece on the shaft, it can thus be placed in the shaft at a location that is preferably readily accessible during and after the implantation (this will often be a central position). This ensures adjustability even after the implantation. Particularly in the case of endoprostheses whose ends are not accessible or whose positioning is effected by prosthetic joints arranged there (for example in the case of a shaft for the femur: the head of a hip prosthesis at the top, and the condyles of a knee prosthesis at the bottom), an orientation in a rotational direction is thus always ensured. Just as important as the ability for rotation, however, is that unintentional further rotation is blocked. The invention unites both functions in one element and thus permits a spatially compact and readily accessible combination of easy adjustability, on the one hand, and secure blocking, on the other hand.

The configuration as a modular element in a modular shaft system also allows the rotation element according to the invention to be retrofitted on existing shaft systems. This considerably extends the range of use.

From the point of view of the patient, the invention offers better adjustability to the individual anatomical circumstances and, if necessary, also permits this at a subsequent stage. Costly follow-up operations can thus be avoided.

The rotation piece is expediently configured such that it corresponds to a lengthening module element of the modular shaft system. In this way, a conventional lengthening element can easily be exchanged for the rotation piece according to the invention. The rotation piece thus fits well into existing modular shaft systems.

The clamping device is expediently configured such that it has a central access for an actuation member for applying and/or releasing the block. A central access is understood here as an attachment means for the actuation member, and one which is not arranged at the start or end of the shaft. By virtue of a central access of this kind, a rotation adjustment can be carried out on the shaft even in the implanted state, namely by access from the side. Specifically in the case of a prosthesis having a long shaft, such a lateral access is generally much more favorable from the anatomical point of view.

A cap nut is preferably provided which, in the inserted state, delimits an inner space of the rotation piece. Such a cap nut permits fastening, on the one hand, and, with its inner space, creates a protected region, on the other hand. There, a chamber is thus formed which is suitable for receiving sensitive bearing components, as will be explained in more detail further below.

Moreover, the cap nut, with its outer face, expediently forms a part of the jacket of the rotation piece. A compact configuration of small diameter can thus be achieved, such that the endoprosthesis according to the invention is also suitable for use on thinner bones. The cap nut preferably has a smooth and also preferably round jacket, on which coupling elements for a clamping tool are expediently formed. The smooth jacket affords the advantage of minimal irritation of surrounding tissue. This is especially true when the jacket is round. Coupling elements for the clamping tool are expediently integrated in the jacket. In this way, still with minimal irritation of surrounding tissue, a secure coupling of the clamping tool can be obtained. The coupling elements are advantageously arranged offset in the circumferential direction. This permits a simple transfer of the clamping tool to the next coupling element during the actuation and thus minimizes the requirements regarding the width of the access.

Moreover, the cap nut preferably has a central passage through which an element of the plug connection is guided. This element is preferably connected directly to a bearing insert of the rotation adjustment device. Thus, by virtue of the central passage, the force can be routed directly from the plug connection to the bearing, such that the cap nut itself lies outside the actual force path. The bearing insert and the element of the plug connection are preferably configured as a combination, particularly in one piece. This permits a particularly direct force transmission that is reliable and free of play.

Provision is advantageously made that a rotary bearing of the rotation adjustment device is arranged completely in the rotation piece, preferably enclosed in the inner space of the rotation piece. As has already been explained above, said inner space can expediently be created by the inner region of the cap nut. A protected region is thus formed for the rotary bearing. It is thus effectively protected against soiling or contamination. The rotary bearing expediently comprises a bearing journal and a complementary bearing bush, wherein the bearing journal is preferably cylindrical. The cylindrical configuration has the practical advantage that axial displaceability is ensured while maintaining the functionality of the rotary bearing. A slide joint is as it were also integrated in the rotary bearing. Bearing journal and bearing sleeve thus preferably form a fit that is free of play and does not jam. In this way, a high and reliable force transmission is ensured, and yet good rotatability is achieved.

In the inner space, the blocking device expediently has a locking disk which acts on the rotary bearing. The locking disk is expediently configured as a multi-toothed disk. It engages in the rotary bearing and blocks a further rotation. The locking disk is expediently arranged at the bottom of the bearing boxes. It can then act on the end face of the bearing journal. For this purpose, a complementary toothing is preferably arranged on the end face of the bearing journal, with which toothing the locking disk interacts with form-fit engagement in the locked state.

For this purpose, the cap nut is preferably configured such that, in a first, clamped position, it presses the locking disk onto the rotary bearing and thus blocks it, and, in a second, open position, the locking disk comes free from the rotary bearing, such that the rotary bearing becomes movable. Thus, by an actuation of the cap nut, in particular rotation, the rotary bearing can be secured or released.

In an expedient embodiment, the rotation piece is configured in two parts, with a rotation part and a spacer part. The rotation part comprises the actual rotation adjustment device and the clamping device. The spacer part functions substantially as a preferably exchangeable lengthening element. The spacer part is expediently connected at its end to the rotation piece for conjoint rotation therewith and, at its other end, it has a mating element of the plug connection. The spacer part and/or the bearing insert are preferably replaceable by other ones with a different plug connector. Thus, by replacing these two components, the rotation piece according to the invention can be adapted to other plug connections. A much wider range of use is thus achieved.

BRIEF DESCRIPTION OF THE DRAWINGS

The invention is explained in more detail below on the basis of an advantageous illustrative embodiment and with reference to the drawing, in which:

FIGS. 1a-c show side views of a modular shaft system for a femur, with rotation piece in different phases;

DETAILED DESCRIPTION

Figure 2A:
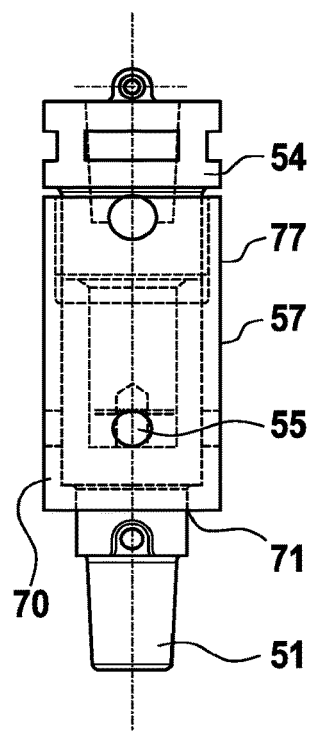
FIGS. 2a-b show a side view and a sectional view of the rotation piece.
Figure 2B:
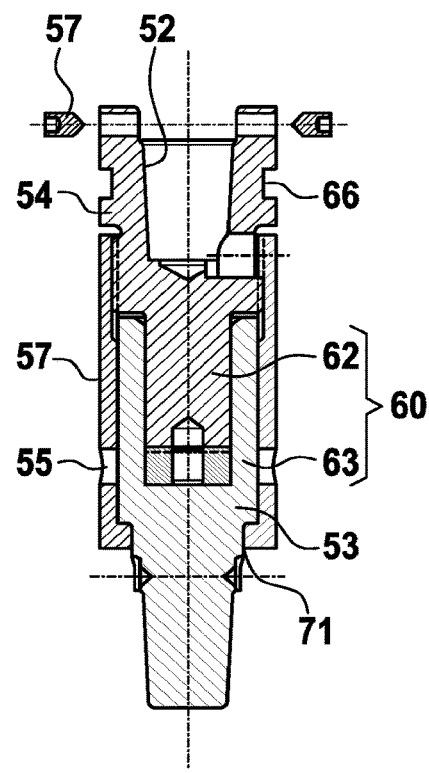
Figure 3:
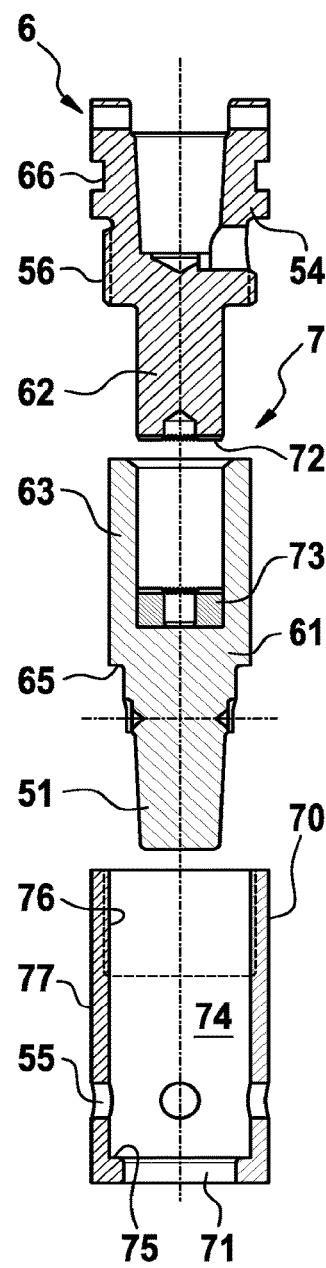
FIG. 3 shows an exploded sectional view of the rotation piece.

The figures depict a modular shaft system for insertion into and partial replacement of a femur.

The modular shaft system has a shaft 1 with, arranged at its lower end, a condylar joint component 2 of a knee joint endoprosthesis. An anchor 3 in the femoral head is provided at the upper end, wherein in the present case the anchor 3 is configured as a cancellous bone screw.

The shaft 1 is provided in a modular configuration composed of a plurality of module elements. It comprises, in the upper region, an anchoring part 10 for anchoring in the medullary canal of an upper part of the femoral bone, and a modular lengthening part 4 in the lower region. The joint component 2 is arranged as further module element on the lengthening part 4. The modular lengthening part 4 is part of a construction kit of different lengthening pieces, which can have different lengths.

An illustrative embodiment of a rotation piece 5 according to the invention is arranged between the anchoring part 10 and the lengthening part 4. It is connected in a load-bearing manner both to the lengthening part 4 and to the anchoring part 10 via a plug connection 45. A further plug connection can be arranged between the lengthening part 4 and the joint component 2.

During the assembly of the prosthesis, a defined angular position has to be adopted relative to the femoral bone 9. It is defined in the upper region by the orientation of the anchoring element 3, and it is defined in the lower region by the orientation of the joint component 2 forming the upper part of a knee joint endoprosthesis. Firstly, the anchoring part 10 is inserted into the medullary cavity of the femoral bone 9, and a receiving channel 93 for the anchoring element 3 is drilled in the region of the head of the femoral bone 9. The prosthesis with the rotation element 5, the lengthening part 4 and the joint component 2 is then assembled. In the next step, the anchoring element 3 is inserted and the prosthesis is thus fixed in terms of it angular position relative to the femoral bone 9. In the further course of the operation, it is then necessary to align the joint component 2 for its intended use as an element of the knee joint prosthesis. For this purpose, its rotational position has to be adapted. This is done using a suitable tool 8 with which the rotation piece 5 is rotated and is blocked in the rotated position.

The structure and the functioning of the rotation piece 5 are explained below. The rotation piece 5 comprises a rotation adjustment device 6 for adjusting a rotation, and also a clamping device 7 for blocking the adopted rotation. The upper region and lower region of the rotation piece 5 are in this case rotated relative to each other, with the result that the joint component 2 is rotated relative to the anchoring part 10. The position adopted by such a rotation is also designated as the "rotation position". The angle by which such a rotation is performed is designated as the rotation angle α (cf. FIG. 5b).

The rotation adjustment device 6 comprises a rotary bearing 60 consisting of a bearing journal 62 and a bearing bush 63. The bearing journal 62 is arranged on a main body 54, while the bearing bush 63 is arranged on a bearing insert 61. The bearing journal 62 is cylindrical, and the bearing bush 63 is configured accordingly as an adapter sleeve for the bearing journal 62, such that the latter is mounted therein in a manner free of play and without jamming. The bearing journal 62 is different in the axial direction to the bearing insert 61. A conical sleeve 52 of the plug-in connection 45 is formed on the main body 54, on the side lying opposite the bearing journal 62. The main body 54 thus forms the upper region of the rotation adjustment device 6.

On its side lying opposite the bearing bush 63, the bearing insert 61 has a conical stub 51 of the plug-in connection 45. The bearing insert 61 thus forms the lower region of the rotation adjustment device 6. The desired rotation in the shaft 1 can be effected by rotating the bearing insert 61 relative to the main body 54. To make this easier, flat regions 66 are formed on the main body 54 and serve as receptacles for a tool wrench 81. The main body 54 can thus be rotated. In this way, a desired rotation angle α can be adopted.

In order to block the rotation position thus adopted, the blocking device, which is a portion of the clamping device 7 is provided. The latter comprises a cap nut 70 with a central passage 71. Within its interior, it has an inner space 74, of which the inner wall is provided, at the end opposite the passage 71, with an inner thread 76 which, in the inserted state, comes into engagement with a complementary outer thread 56 provided on the main body 54. Within the cap nut 70, a chamber 74 is formed which is connected to the passage 71. In the inserted state, the cap nut 70 is pushed with its passage 71 over the conical stub 51 of the bearing insert 61, specifically until the inner thread 76 engages in the outer thread 56. The cap nut can thus be tightened by rotation, as a result of which the clamping device 7 is actuated (or, by rotation in the opposite direction, released). In the region of the passage 71, a shoulder 75 is formed which acts on a collar 65 on the bearing insert 61. By tightening the cap nut 70, the latter screws farther onto the thread 56, 76 and thus moves in the direction of the main body 54, as a result of which the shoulder 75 acts on the collar 65 of the bearing insert 61 and carries this with it. The latter is thus likewise moved toward the main body 54, specifically until a multi-toothed locking disk 73 arranged, for conjoint rotation, at the bottom of the bearing bush 63 engages in a complementarily shaped mating disk 72, which is arranged for conjoint rotation at the tip of the bearing journal 62. Thus, by tightening of the cap nut 70, the multi-toothed disk 73 and the mating disk 72 mesh with each other, such that a further rotation of the bearing bush 63 relative to the bearing journal 62 is prevented. The clamping device 7 is thus actuated and blocks the rotary bearing 60 against undesired rotation. By loosening of the cap nut 70, the clamping device 7 can be correspondingly released, in order thereby to again permit a rotation of the rotary bearing 60.

With its inner space 74, the cap nut 70 forms an enclosure for the rotary bearing 60. The latter is thus protected against ingress of foreign bodies and contaminants, which could otherwise compromise a perfect bearing function.

On its jacket 77, the cap nut 70 moreover has a plurality of radial openings offset in the circumferential direction and functioning as coupling elements 55 for an actuation tool 80. The latter has, on its head, corresponding projections (not shown) which engage with positive locking in the coupling elements 55 and thus permit an actuation of the cap nut 70 through rotation. By means of the tool 80 being placed onto the flattened region 66 of the main body 54, it is possible, if necessary, to hold the rest of the shaft free of force.

Figure 4:
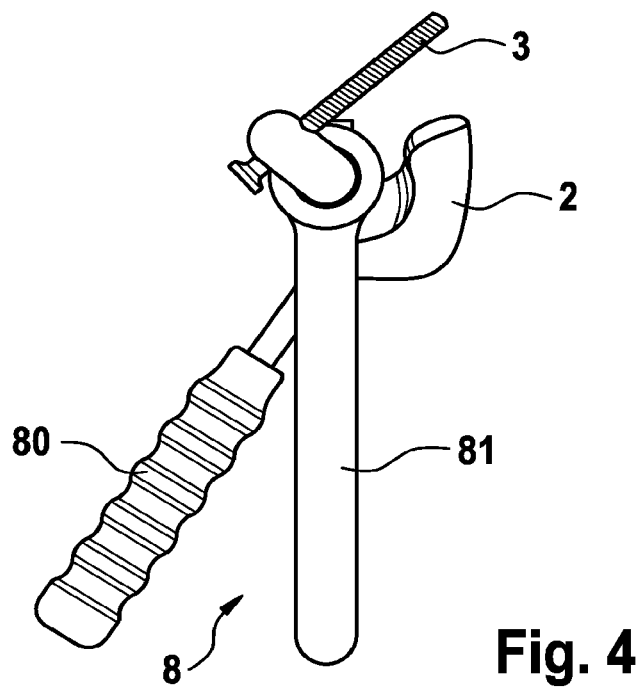
FIG. 4 shows a plan view of the modular shaft with a tool for clamping and adjusting the rotation.
Figure 5A:
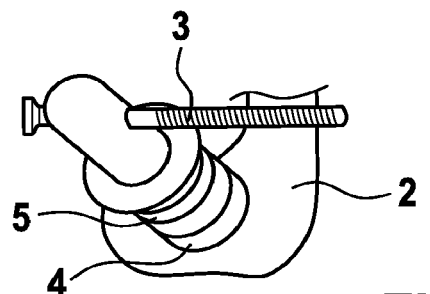
FIGS. 5a-b show views depicting the state of the modular shaft before and after the rotation.
Figure 5B:
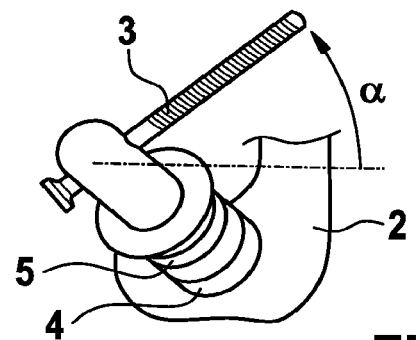

This procedure of applying the two tools 80, 81 is shown in FIG. 4, in order thereby to release the clamping device 7 and permit a mutual rotation of the joint component 2 relative to the upper shaft part with the anchoring element 3. Such a rotation about a rotation angle α is shown in FIGS. 5a and 5b.

The self-contained rotation piece 5, with the rotation element 6 arranged therein and the clamping device 7, thus permits in a compact manner a rotation of the shaft, on the one hand, and an effective blocking against undesired adjustment, on the other hand, wherein actuation from the side via the jacket surface 77 permits access that is favorable from the handling point of view. This access is referred to in the present case as a central access, in contrast to the access via the ends of the shaft.

Moreover, in a variant of the invention, a two-part configuration can be provided in which a spacer part is arranged fixedly on the actual rotation piece 5. The spacer part is configured like a short lengthening piece with a stub connection at its end faces, i.e. a stub cone at one end and a stub sleeve at the opposite end face. It is inserted with its stub cone into the stub sleeve 52 of the rotation piece 5. By way of the resulting plug connection 45, and also by means of the grub screws 57 functioning as an additional blocking means, the spacer part is connected fixedly to the rotation piece 5. In this way, the length can be varied solely by replacing the spacer part, without having to make any structural modification to the rotation piece 5 itself; the rotation piece 5 itself can remain unchanged. Adaptation of the rotation piece 5 to different modular systems is thus made much easier.

The invention claimed is:

1. An endoprosthesis shaft system for elongate bones, comprising:
   an anchoring part; and
   a shaft, which is formed from module elements that can be coupled by means of a plug connection,
   wherein a mutual rotation of the elements along the shaft is adjustable and is blocked by means of an anti-rotation mechanism, and
   wherein, in order to adjust the rotation, a rotation piece is provided as a further module element, which has a self-contained rotation adjustment device and a clamping device as a means for blocking the rotation, wherein the rotation piece has two end faces, for the plug connection, and a jacket, wherein the self-contained rotation adjustment device comprises a distal end and a proximal end, the distal end configured to extend into a portion of the jacket, wherein a perimeter of the distal end is smaller than a diameter of the proximal end.

2. The endoprosthesis shaft system comprising a modular shaft system as claimed in claim 1, wherein the rotation piece functions as a lengthening module element.

3. The endoprosthesis shaft system as claimed in claim 1, wherein the clamping device has a central access for an actuation member for applying/releasing the block.

4. The endoprosthesis shaft system as claimed in claim 1, wherein an access for adjusting the anti-rotation mechanism is provided through an opening of the jacket.

5. The endoprosthesis shaft system as claimed in claim 1, wherein a cap nut is provided which, in an inserted state, delimits an inner space of the rotation piece.

6. The endoprosthesis shaft system as claimed in claim 5, wherein the cap nut has a smooth jacket on which coupling elements for a clamping tool are formed.

7. The endoprosthesis shaft system as claimed in claim 6, wherein the cap nut has a round jacket and wherein the coupling elements are arranged offset in a circumferential direction.

8. The endoprosthesis shaft system as claimed in claim 5, wherein the cap nut has a central passage through which an element of the plug connection is guided, wherein the element is connected directly to a bearing insert of the rotation adjustment device.

9. The endoprosthesis shaft system as claimed in claim 8, wherein the bearing insert and an element of the plug connection are combined.

10. The endoprosthesis shaft system as claimed in claim 5,
wherein a rotary bearing of the rotation adjustment device is arranged completely in the rotation piece,
wherein the clamping device further comprises a locking disk which acts on the rotary bearing and which is arranged in an inner space at a bottom of a bearing bush, and
wherein the cap nut, in a first, clamped position, presses the locking disk onto the rotary bearing and thus blocks it, and, in a second, open position, the locking disk comes free from the rotary bearing, such that the rotary bearing is movable.

11. The endoprosthesis shaft system as claimed in claim 5, wherein the cap nut, with its outer face, forms a part of the jacket of the rotation piece.

12. The endoprosthesis shaft system as claimed in claim 1, wherein a rotary bearing of the rotation adjustment device is arranged completely in the rotation piece.

13. The endoprosthesis shaft system as claimed in claim 12, wherein the rotary bearing comprises a cylindrical bearing journal and a complementary bearing bush, wherein the bearing journal and a bearing sleeve form a fit that is free of play and does not jam.

14. The endoprosthesis shaft system as claimed in claim 12, wherein the clamping device further comprises a locking disk which acts on the rotary bearing and which is arranged in an inner space at a bottom of a bearing bush.

15. The endoprosthesis shaft system as claimed in claim 12, wherein the rotation piece is configured in two parts, with an attached spacer part.

16. The endoprosthesis shaft system as claimed in claim 15, wherein the spacer part is at one end connected to the rotation piece for conjoint rotation therewith and, at its other end, carries a mating element of the plug connection.

17. The endoprosthesis shaft system as claimed in claim 16, wherein a rotary bearing of the rotation adjustment device is arranged completely in the rotation piece, and
wherein the spacer part and/or the bearing insert are replaceable by other ones with a different plug connector.

18. The endoprosthesis shaft system as claimed in claim 1, wherein a portion of the rotation adjustment device is configured to thread into a portion of the jacket.

19. The endoprosthesis shaft system as claimed in claim 1, wherein an access for adjusting the anti-rotation mechanism is provided through an opening of the jacket.

20. The endoprosthesis shaft system as claimed in claim 1, wherein a rotary bearing of the rotation adjustment device is arranged completely in the rotation piece.

* * * * *